United States Patent [19]

Goldberg et al.

[11] 4,180,558

[45] Dec. 25, 1979

[54] UNIT DOSAGE FORMS

[75] Inventors: Arthur H. Goldberg, Montclair; Michael L. Franklin, Parsippany, both of N.J.

[73] Assignee: Hoffmann-La Roche Inc., Nutley, N.J.

[21] Appl. No.: 935,274

[22] Filed: Aug. 21, 1978

[51] Int. Cl.$^2$ .......................... A61K 9/70; B32B 31/18
[52] U.S. Cl. ...................................... 424/16; 128/260; 424/28; 428/534
[58] Field of Search ................... 128/260; 424/16, 27, 424/28; 428/534

[56] References Cited

U.S. PATENT DOCUMENTS 4,029,758  6/1977  Mlodozeniec et al. ............ 424/16 X

*Primary Examiner*—Shep K. Rose
*Attorney, Agent, or Firm*—Jon S. Saxe; George M. Gould; R. Hain Swope

[57] ABSTRACT

Use of an improved water-swellable carboxymethylcellulose paper in a unique pharmaceutical unit dosage form comprising a stack of edible webs laminated at the edges at least some of which are paper is described. The subject paper is a superior delaminating agent in said unit dosage forms.

3 Claims, 3 Drawing Figures

UNIT DOSAGE FORMS

STATEMENT OF PRIOR ART

The use of various paper compositions as substrates for the ingestion of a medicament is known in the art. Belgian Pat. No. 637,363 published Mar. 13, 1964 and Netherlands Pat. No.7,507,785 published Jan. 7, 1976 teach incorporation of the medicament into a paper web.

Higuchi et al U.S. Pat. No. 3,625,214 issued Dec. 7, 1971 describes pharmaceutical dosage forms prepared by depositing a matrix containing medicament on a substrate which might be of paper composition and then spirally rolling the coated substrate, e.g. in the manner of a jelly roll.

Finally, a series of U.S. Pats., e.g. No. 4,029,758 issued June 14, 1977 teach specific paper compositions useful in the preparation of a novel, solid unit dosage forms wherein finely divided medicament is loaded to the surface of one or more webs of paper or polymeric composition, and the loaded web(s) is fabricated into an orally ingestible, pharmaceutically and cosmetically acceptable shape and sealed so as to have no exposed medicament.

The latter mentioned patent claims a method of forming solid unit dosage forms wherein a stack of edible webs, e.g. 20 or more are fabricated into a unit dosage form by laminating only the edges. Upon ingestion, the laminated edges rupture thereby, allowing the stack of webs to separate and disperse. As this takes place, finely particulate medicament loaded to at least one of the sheets of web becomes exposed for absorption. In view of the number of sheets utilized in a laminate, the surface area available for absorption from such a unit dosage form is quite large in comparison to conventional dosage forms.

In accordance with the present invention, it has been found that a particular paper formulation, not heretofore suggested for the preparation of such unit dosage forms, possesses unexpectedly superior properties when utilized in the form of one or more sheets in an edge-sealed laminate unit dosage form.

DETAILED DESCRIPTION OF THE INVENTION

Figure 1:
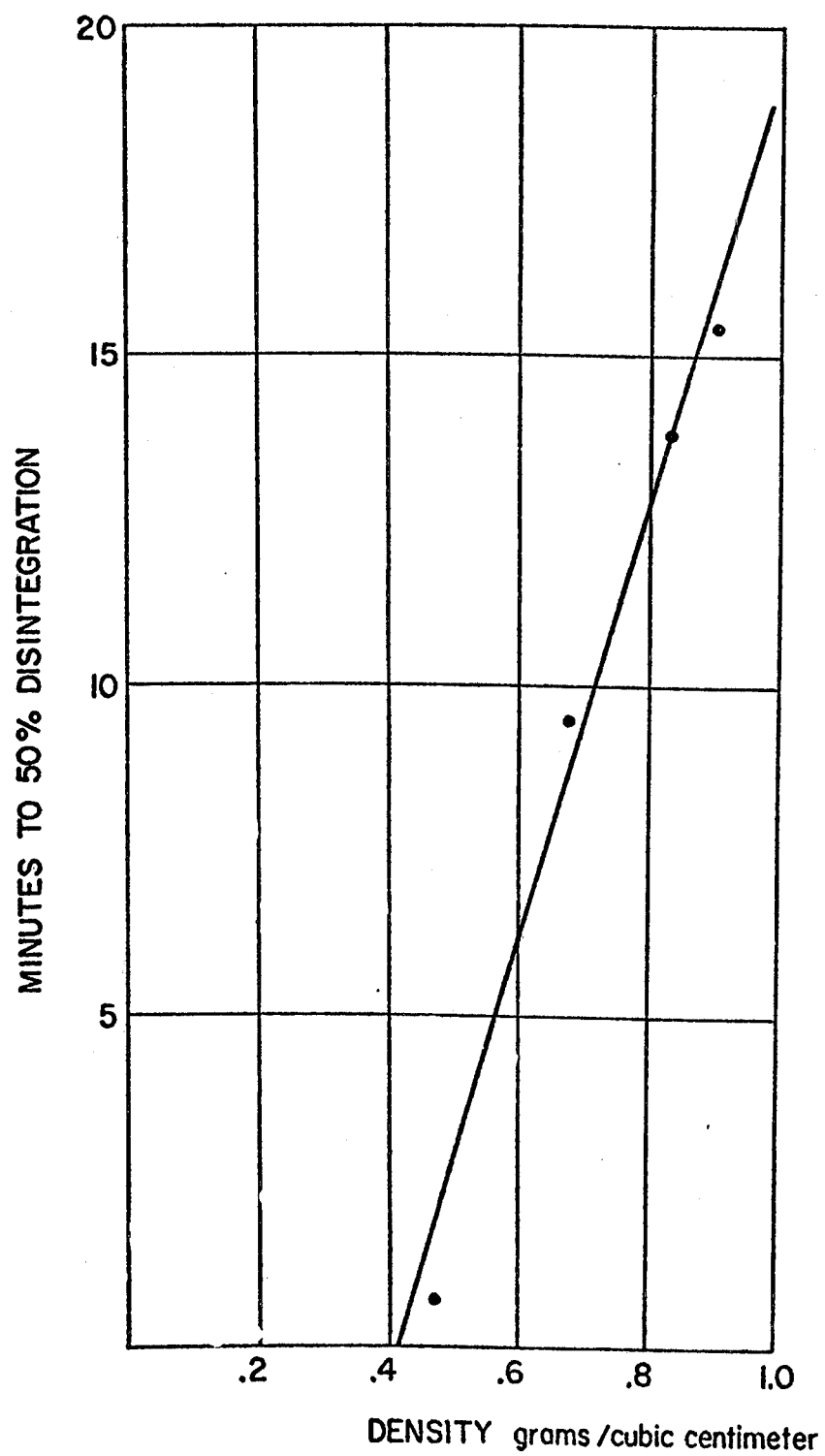
FIG. 1 represents a graph plotting disintegration time of single sheets of the paper composition of the invention as a function of the density of the sheet.

The paper webs utilized in the preparation of edge-sealed laminated unit dosage forms in accordance with the present invention along with a method for their preparation are taught in U.S. Pat. No. 3,826,711 issued July 30, 1974, the disclosure of which is incorporated herein by reference. The materials useful for the manufacture of the paper webs are disclosed in U.S. Pats. 3,589,364; 3,678,031 and 3,379,720, issued June 29, 1971; July 18, 1972 and Apr. 23, 1968 respectively. The disclosure of these patents are also incorporated herein by reference. The disclosed paper webs are coherent of at least partially water-soluble and water-swellable fibers of cellulose derivatives such as sodium carboxymethylcellulose, wet epichlorohydrin cross-linked sodium carboxymethylcellulose or sodium carboxymethylcellulose cross-linked by other means described in said patents. It is critical to the practice of the invention that the final sheets are not more than about 20% by weight soluble in water and preferably from about 2% by weight to about 10% by weight soluble in water. This limitation in water soluble fibers vs. water-swellable fibers is critical to the operation of the paper sheets in the dosage form as will be discussed hereinafter.

The paper webs contemplated herein are prepared with the materials and in accordance with the method described in the above mentioned patents. This method generally comprises forming a slurry of the fibers at a consistency of 0.5% to 3% by weight in an aqueous organic slurry media, e.g. water/methanol, containing from about 32% to 50% by weight water, forming a fibrous sheet from the dispersion on a filter media, washing the sheet in 2 to 5 stages of alcohol displacement washing gradually decreasing the water content of the sheet to about 0.02 to 0.5 part by weight water per part carboxymethylcellulose fiber and drying the resulting sheets. The webs must be uniform both in thickness and width. Generally, the webs should be from about 1 to about 25 mils. (about 0.025 mm. to about 0.64 mm.), preferably from about 3 to about 12 mils. (about 0.076 mm. to about 0.305 mm.) thick. The width of the web can be of any convenient size, for example 12 inches (30 cm.). The width of the web can be adjusted to the particular equipment being utilized. Likewise, the length of the web is not critical. Because the contemplated unit dosage forms are amenable to high speed manufacture webs are conveniently prepared in large quantity, e.g. 1500 feet or more, and stored, e.g. on cores or spools.

The improved edge-sealed laminates of the present invention are formed in accordance with the methods described in U.S. Pat. No. 4,029,758. For example, a suitable stack of webs can be continuously passed through a pair of heated reciprocating die plates which would form, seal and cut dosage forms simultaneously from the moving stack.

The stack of webs in the contemplated laminate may be predominantly sheets of edible polymeric material, sheets of edible paper or equal mixtures thereof. The edible polymeric webs are formed from a composition which, in general, comprises:

(a) One or more organic film formers, i.e. art-recognized, non-toxic film formers such as, for example, natural and chemically modified starches and dextrins, cellulose derivatives such as hydroxypropyl cellulose, sodium carboxymethylcellulose and the like, other polysaccharides such as pectin, acacia and the like, synthetics such as polyvinylpyrrolidone, polyvinylalcohol and the like. Preferred film formers are hydroxypropylcellulose and sodium carboxymethylcellulose;

(b) One or more plasticizers such as those recognized in the art of pharmaceutical compounding, for example, glycerin, the polysorbates, certain mixtures of mono- and di-glycerides of saturated fatty acids and the like;

(c) Modifiers, i.e. ingredients optional with certain formulations such as disintegrants, extenders, pigments and the like; and one or more fugitive solvents, e.g.

water, lower alkanols such as methanol, ethanol and the like.

The polymeric formulations contain from about 5% by weight to about 95% by weight, preferably from about 40% by weight to about 90% by weight film former, from about 1% by weight to about 60% by weight, preferably from about 10% by weight to about 50% by weight plasticiser and from about 0% by weight to about 40% by weight of said modifiers, e.g. a disintegrant.

The edible paper webs other than those contemplated herein are formed from a composition which, in general, comprises:

(a) One or more fibrous materials such as, for example, cotton, linen cellulose, textured vegetable protein, preferably hardwood or softwood fibers or mixtures thereof;

(b) One or more non-fibrous modifiers, i.e. ingredients optional with certain formulations such as organic film formers such as enumerated above, disintegrants, extenders and the like; and (c) A fugitive solvent, e.g. water, a lower alkanol such as methanol, ethanol, isopropanol and the like.

Preferred paper formulations comprise from about 70% by weight to about 99% by weight, preferably from about 90% by weight to about 96% by weight fibers, from about 1% by weight to about 30% by weight, preferably from about 4% by weight to about 10% by weight of a binder/disintegrant such as, for example, hydroxypropylcellulose, sodium carboxymethylcellulose, polyvinylpyrrolidone and the like, and from about 0% by weight to about 5% by weight, preferably from about 0% by weight to about 2% by weight of an edible surfactant such as, for example, polysorbate 80, dioctyl sodium sulfosuccinate and the like.

The paper webs are formed by conventional methods and on conventional apparatus such as, for example, the Fourdrinier paper making machines. The polymeric webs are also formed by methods conventional in the art, e.g. by casting on a suitable substrate such as Mylar, stainless steel, release paper or the like and then dried. The polymeric webs can also be formed by conventional extrusion techniques where the film forming component is amenable to such techniques, e.g. hydroxypropylcellulose.

The improved paper sheets utilized in edge-seal laminated pharmaceutical unit dosage forms in accordance with the present invention function unexpectedly to both seal the edges of the dosage form through the application of heat and pressure and to delaminate the unit dosage forms in the stomach. The capability of the paper sheets contemplated herein to function as delaminating sheets and therefore to disintegrate unit dosage forms incorporating them in the stomach can be controlled by altering the physical properties of the sheets. Therefore the capacity of sheets of identical chemical composition to function as delaminating agents can be altered by techniques such as calendering, basis weight control or other means known to those skilled in the paper arts. By the use of these techniques, one can control the density of the sheets.

Figure 2:
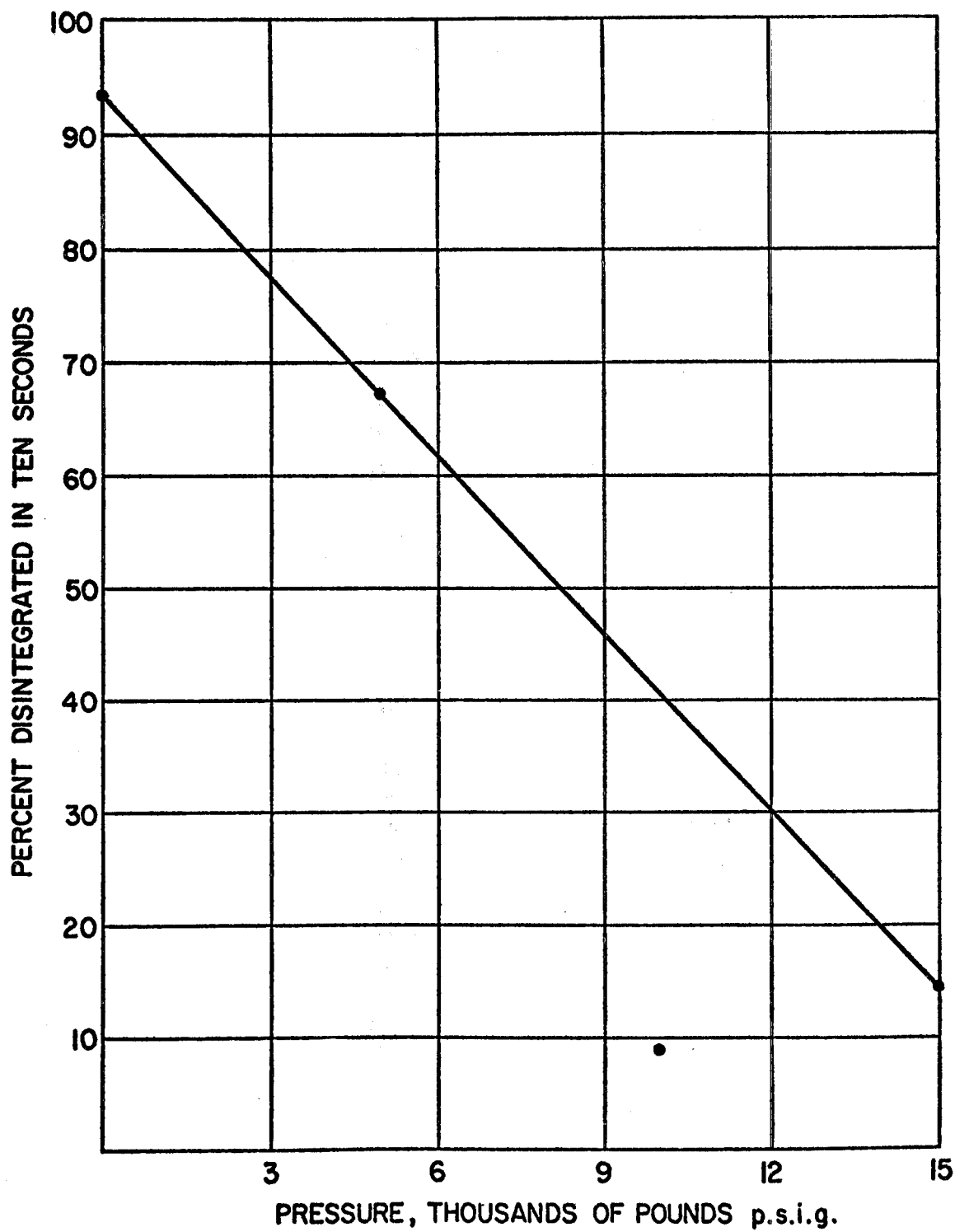
FIG. 2 represents a graph plotting percent disintegration of single sheets of the paper composition of the invention in ten seconds as a function of the pressure applied to the sheet.
Figure 3:
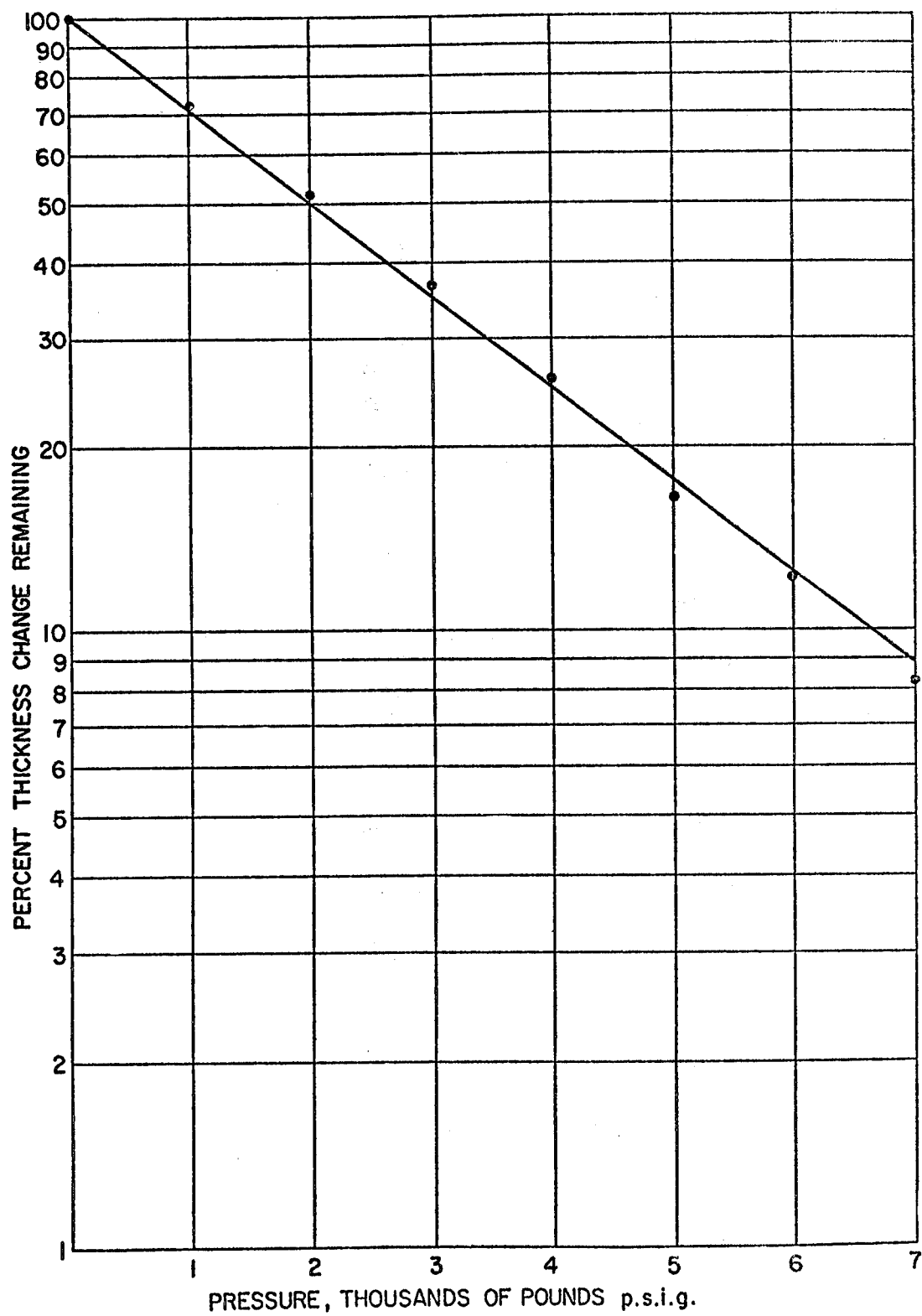
FIG. 3 represents a graph plotting the thickness change remaining in single sheets of the paper composition of the invention as a function of the pressure applied to the sheet.

As is evident from FIG. 1, one can control the rate of disintegration of the cross-linked carboxymethylcellulose sheets utilized in the present invention by adjusting the density of the sheet. It is further evident from FIG. 2 that the disintegration rate of the sheet is also related to the pressure in the calender stack. It can be seen from FIG. 3 that the thickness of the sheet can be calculated from the log normal effect of pressure, which is easily translatable into sheet density.

In addition, when conventional, untreated paper is incorporated into edge seal laminated pharmaceutical unit dosage forms as contemplated herein by a single application of heat and pressure utilizing heated dies that simultaneously form a plurality of unit dosage forms, many do not form cohesive units. Many of the unit dose forms that are formed exhibit splitting of the edges, e.g. in transit. Introduction of between about 2 and about 15 layers of the cross-linked carboxymethylcellulose paper as described herein into such unit dosage forms markedly increases the number of cohesive dosage units formed and reduces or eliminates the incidence of split edges in the finished unit dosage forms.

The above described dual functions are considered prepared by the method described in U.S. Pat. No. 3,826,711, i.e. a coherent fibrous sheet product formed from an aqueous alcoholic fibrous slurry comprised of at least partially water-soluble and water-swellable carboxymethylcellulose fibers, which has a communition quality of from about 0.1 to 30 and a water solubility not in excess of 20% is not known as being capable of precise swelling and disintegration as a function of the density of the sheet. Also, it is considered unexpected that, as applicants have found, stacks of this paper can be edge sealed by the application of heat and pressure. It has been found in accordance with the present invention that such sheets do in fact seal not only themselves but layers of conventional paper as well, and do in fact swell and disintegrate under the acid conditions of the stomach, and that the swelling and disintegrating properties are controllable post-manufacture by physical alteration of the sheet. It has further been found that, unexpectedly, edge-seal laminates such as described herein containing such sheets disrupt, thereby making the medicament contained therein available for absorption at a substantially enhanced rate over similar unit dosage forms which do not contain them. The capacity of the sheets to disrupt can be controlled by controlling pressure on the sheet thereby releasing the medicament from the unit dosage forms at any desired release rate pattern.

Two different mechanisms are contemplated herein for controlling the rate of release of medicament from edge seal laminated unit dosage forms are contemplated herein. The first of these is the use of the improved carboxymethylcellulose paper sheets described herein solely as a means to separate the medicament loaded sheets from the body of the edge-seal laminates. In this instance, the medicament will be loaded to sheets of conventional paper. In the stomach, the sheets of the improved paper composition function to delaminate the unit dosage forms. The second method utilizes the improved paper composition sheets both as delaminating and disintegrating means. In this instance, the medicament is loaded to the improved paper composition sheets, i.e. the sheet serves as a substrate for the medicament. The medicament loaded sheets are separated in the unit dosage form by sheets of non-loaded, conventional paper.

It has been found in accordance with the present invention that the laminates described herein, which generally contain from 5 to 60 sheets, preferably from 8 to 32 sheets, must contain the improved sheets as described herein in a ratio of at least one improved sheet for every medicament loaded sheet in the laminate, regardless of whether the remaining sheets are of a paper or polymeric composition. While it is in theory possible to have a laminate totally comprised of such improved sheets, in general a maximum content will be one improved sheet for every medicament loaded sheet therein. The improved sheets are randomly dispersed throughout the laminate, preferably evenly dispersed. The improved sheets may or may not have medicament loaded thereto as described in said U.S. Pat. No. 4,029,758. As a sealer layer, from about 1 to 20 sheets, preferably from about 3–8 sheets of the improved paper are utilized. The inclusion of these sheets in the unit dosage forms contemplated herein materially reduces delaminating and/or edge splitting in storage or transit.

By utilizing the improved sheets as described herein in an edge-sealed laminate unit dosage form, it is possible to achieve improvement both in rate an uniformity of release of medicament from such unit dosage forms in the stomach.

EXAMPLE 1

Edge-seal unit dosage forms were prepared by stacking twenty sheets of various paper composition webs as set forth below and subjecting them to heated reciprocating dies at a pressure of 13,000 lbs. p.s.i.g.

Coating layer
Cross-linked CMC layer
Medicament loaded layer
Cross-linked CMC layer
Sealing layers (12)
Cross-linked CMC layer
Medicament loaded layer
Cross-linked CMC layer
Coating layer The coating layer comprised a conventional paper composition webs impregnated with 5% by weight sodium carboxymethylcellulose. The medicament loaded layers were conventional paper composition webs dry coated with chlorodiazepoxide. The sealing layers were conventional paper composition webs impregnated with hydroxypropylcellulose.

In the above lamination, the cross-linked CMC layer functioned to delaminate the medicament loaded layers from the sealing sheets in the stomach, i.e. artificial gastric fluid.

EXAMPLE 2

In accordance with the procedure described in Example 1, edge-seal unit dosage forms were prepared from the following stack of webs.

Coating layer
Medicament loaded cross-linked CMC layer
Non-disintegrating filler layer
Medicament loaded cross-linked CMC layer
Non-disintegrating filler layer
Sealing layers (10)
Non-disintegrating filler layer
Medicament loaded cross-linked CMC layer
Non-disintegrating filler layer
Medicament loaded cross-linked CMC layer
Coating layer The medicament utilized was chlordiazepoxide. The non-disintegrating filler layer was a conventional web comprised of cellulose fibers. The cross-linked CMC layer functioned in this laminate as both as substrate and a delaminating layer.

EXAMPLE 3

In accordance with the procedure of Example 1, edge-seal unit dosage forms were prepared from the following stack of webs.

Coating layer
Cross-linked CMC layer
Medicament loaded layer
Cross-linked CMC layer
Non-disintegrating filler layer
Cross-linked CMC layers (10)
Non-disintegrating filler layer
Cross-linked CMC layer
Medicament loaded layer
Cross-linked CMC layer
Coating layer In this lamination the ten internal cross-linked CMC layers functioned to seal the unit dosage form and the interspersed cross-linked CMC layers functioned to delaminate the unit dosage form.

We claim:

1. In a solid pharmaceutical unit dosage form comprising a laminate composed of a plurality of layers of an edible, therapeutically inert web, at least one of said layers having one or more medicaments loaded on to one or more surfaces, said layers of web arranged in said laminate so that substantially no medicament is loaded to an outer surface thereof, said laminate being sealed only at the edges so as to completely internalize said medicament, the improvement which comprises controlling the dissolution rate of said laminate by including therein at least one web of an improved paper composition formed from an aqueous alcholic fibrous slurry and consisting essentially of water-soluble carboxymethylcellulose fibers and water-insoluble, water-swellable, cross-linked carboxymethylcellulose fibers, said web by not greater than 20% soluble in water, the rate of disolution of said laminate being directly related to the density of said web of improved paper composition.

2. The improved laminate in accordance with claim 1 wherein for each 1 to 3 layers of web having medicament loaded thereto in said laminate there is present one layer of said improved web.

3. The improved laminate in accordance with claim 1 wherein there is present two layers of said improved web for each layer of web having medicament loaded thereto in said laminate.

* * * * *